United States Patent [19]

Sweetser

[11] 4,343,649

[45] Aug. 10, 1982

[54] HERBICIDE ANTIDOTES

[75] Inventor: Philip B. Sweetser, Wilmington, Del.

[73] Assignee: E. I. Du Pont de Nemours and Company, Wilmington, Del.

[21] Appl. No.: 207,734

[22] Filed: Nov. 17, 1980

[51] Int. Cl.[3] .......... A01N 25/32

[52] U.S. Cl. .......... 71/93; 71/92

[58] Field of Search .......... 71/92, 93

[56] References Cited

U.S. PATENT DOCUMENTS

| | | | |
|---|---|---|---|
| 3,564,768 | 2/1971 | Hoffmann | 71/100 X |
| 3,702,759 | 11/1972 | Hoffmann | 71/77 |
| 3,749,566 | 7/1973 | Hoffmann | 71/100 |
| 4,021,224 | 5/1977 | Pallos et al. | 71/88 |
| 4,070,389 | 1/1978 | Martin | 71/93 |
| 4,124,376 | 11/1978 | Pallos et al. | 71/118 |
| 4,127,405 | 11/1978 | Levitt | 71/93 |
| 4,137,070 | 1/1979 | Pallos et al. | 71/100 |
| 4,169,719 | 10/1979 | Levitt | 71/92 |

OTHER PUBLICATIONS

Hoffman, Chemistry and Action of Herbicide Antidotes, pp. 10–13, Academic Press, (1978).

Stephenson et al., Chemistry and Action of Herbicide Antidotes, pp. 41, 43, Academic Press, (1978).

Parrier et al., Proc. 1980 British Crop Protection Conf. Weeds.

*Primary Examiner*—Catherine L. Mills

[57] ABSTRACT

Cereal crops can be protected from damage caused by certain sulfonylurea herbicides by application of an antidotal compound selected from 1,8-naphthalic anhydride, α-(cyanomethoxyimino)benzacetonitrile, and N,N-diallyl-2,2-dichloroacetamide.

15 Claims, No Drawings

HERBICIDE ANTIDOTES

BACKGROUND OF THE INVENTION

The compounds 2-chloro-N-[(4-methoxy-6-methyl-1,3,5-triazin-2-yl)aminocarbonyl]benzenesulfonamide, 2,5-dichloro-N-[(4,6-dimethoxypyrimidin-2-yl)aminocarbonyl]benzenesulfonamide and 2-carbomethoxy-N-[(4,6-dimethylpyrimidin-2-yl)aminocarbonyl]-benzenesulfonamide are known to be potent herbicides. These compounds and their herbicidal utility are disclosed, respectively, in U.S. Pat. No. 4,127,405, dated Nov. 28, 1978, U.S. Pat. No. 4,169,719, dated Oct. 2, 1979, and unexamined European Patent Application No. 7687, published Feb. 6, 1980. The disclosure of these two patents and of the patent application are hereby incorporated by reference.

It is often difficult to find herbicidal compounds which exhibit sufficient selectivity, that is, which will control weeds but which will not damage useful crop plants. In many cases, antidotes have been found which, when applied in combination with a particular herbicide, act to protect the useful crop plant from damage caused by the herbicide but which do not adversely affect the action of the herbicide on weeds.

U.S. Pat. No. 3,564,768, dated Feb. 23, 1971, discloses that 1,8-naphthalic anhydride can be applied to corn seeds to protect corn plants from damage caused by N,N-dialkylthiocarbamate ester preemergent herbicides. According to U.S. Pat. No. 3,749,566, dated July 31, 1973, 1,8-naphthalic anhydride is also useful for protecting rice from N,N-dialkylthiocarbamate ester herbicide damage.

U.S. Pat. No. 4,070,389, dated Jan. 24, 1978, discloses that α-(cyanomethoxyimino)benzacetonitrile protects crops from damage caused by triazine, phenylurea, carbamate, benzoic acid derivative and halogenphenoxyacetic acid herbicides.

U.S. Pat. No. 4,021,224, dated May 3, 1977, U.S. Pat. No. 4,124,376, dated Nov. 7, 1978, and U.S. Pat. No. 4,137,070, dated Jan. 30, 1979, disclose the use of N,N-diallyl-2,2-dichloroacetamide as an antidote for thiocarbamate and halo acetanilide herbicides.

SUMMARY OF THE INVENTION

It has now been found that cereal crops can be protected from injury due to an herbicidal compound selected from 2-chloro-N-[(4-methoxy-6-methyl-1,3,5-triazin-2-yl)aminocarbonyl]benzenesulfonamide, 2,5-dichloro-N-[(4,6-dimethoxypyrimidin-2-yl)aminocarbonyl]-benzenesulfonamide and 2-carbomethoxy-N-[(4,6-dimethylpyrimidin-2-yl)aminocarbonyl]benzenesulfonamide by combining application of said herbicide to the locus of said crop plant with application of a non-phytotoxic antidotally effective amount of an antidotal compound selected from 1,8-naphthalic anhydride, N,N-diallyl-2,2-dichloroacetamide, and α-(cyanomethoxyimino)benzacetonitrile to the crop seed, to the crop plant or to the locus of the crop plant. Also included in this invention are herbicidal compositions comprising an herbicidally effective amount of one of the aforementioned herbicides and a non-phytotoxic antidotally effective amount of one of the aforementioned antidotes.

DETAILED DESCRIPTION

Crops which can be protected from injury as described herein include, cereal crops, for example, corn, wheat, rice and sorghum. Application of a non-phytotoxic antidotally effective amount of the antidotes described herein to the crop seed, to the crop plant or to the locus of the crop plant serves to protect the crop plant from damage caused by the herbicides described herein while not adversely affecting the action of the herbicide on desired weeds.

A number of methods are available for combining application of the herbicidal and antidotal compounds described herein. The herbicide and antidote may be applied preemergence (applied to the soil after planting, but before crop plants emerge), by preplant soil incorporation (applied to the soil and mixed into the soil before planting), or postemergence (applied to the emerged crop and/or weeds and on the exposed soil surface). Postemergence treatments may be directed so that the herbicide and/or antidote is applied primarily to the weeds or crop. The antidotes and herbicides may be applied either simultaneously or sequentially, with the antidote application either preceding or following the herbicide application. In addition, the antidote may be applied directly to the crop seed. The seeds may be uniformly coated with the antidote according to standard seed treating procedures prior to planting. Alternatively, the antidote may be applied over the exposed seed in open furrow at planting, just prior to covering the seed with soil (in-the-row treatment).

The ratio of antidote to herbicide used will vary, depending upon the specific antidote and herbicide used and on the method of application used. The crop species and cultural practices may also have an effect. For example, when the antidote is applied as a seed coating, it may be applied at a rate of about 0.1 to 0.5% of the seed weight. When the seeds are planted at from 10 to 150 kg/ha, the antidote would be distributed at from 0.01 to 0.75 kg/ha. In preemergence, preplant soil incorporation and postemergence treatments, the antidote may be applied at about 0.1 to 10 kg/ha. Similar rates may be used for in-the-row treatments; however, since only the furrow is treated, the lower per hectare rate would be diminished to as low as about 0.01 kg/ha, depending upon the row spacing. Since the herbicides may be used at rates of about 0.001 to 2 kg/ha, the ratio of antidote to herbicide may vary between 1:200 and 10,000:1. One skilled in the art could determine the proper ratio to use in a given situation.

In Examples 1 through 11, the crops were typically planted in a silt loam soil at a depth of about 1.5 cm. Spray treatments were applied in an acetone-water-surfactant carrier or, where the component was suitably formulated, in water at a volume rate of about 560 kg/ha. Seed treatments were dissolved or suspended in a carrier consisting of a dimethylformamide-acetone mixture (DMF:acetone, 1:10) which was then added to the seed in a glass container at 2.5 ml per grams of seed. The mixture was tumbled until seeds were uniformly covered and the side of the glass container was clear. Seeds were then aerated thoroughly before planting. Immediately after planting and treating in all but postemergence treatments, the test containers were given simulated rainfall of about 3 mm of water over a 90 minute period to activate the chemical treatments and to initiate crop germination. The tests were then held in the greenhouse under standard greenhouse care until evaluation after from three to seven weeks, depending on the test. Herbicide injury was rated on a scale of 0 to 10 in which 0 indicated no injury, 1 minimal injury and 10 indicated that the plants were dead.

In the following examples, the herbicidal and antidotal compounds are referred to by number as follows:

Ia—1,8-naphthalic anhydride
Ib—α-(cyanomethoxyimino)benzacetonitrile
Ic—N,N-diallyl-2,2-dichloroacetamide
IIa—2-chloro-N-[(4-methoxy-6-methyl-1,3,5-triazin-2-yl)aminocarbonyl]benzene sulfonamide
IIb—2,5-dichloro-N-[(4,6-dimethoxypyrimidin-2-yl)aminocarbonyl]benzenesulfonamide
IIc—2-carbomethoxy-N-[(4,6-dimethylpyrimidin-2-yl)aminocarbonyl]benzenesulfonamide.

The following abbreviations are also used to indicate the various methods of treatment discussed above:

PRE—preemergence
PPI—preplant soil incorporation
POST—postemergence
SEED—seed coating
ROW—in-the-row treatment.

EXAMPLE 1

| | | | Corn Injury Rating (After 4 weeks) | |
|---|---|---|---|---|
| | | | | Antidote |
| Herbicide | kg/ha | Herbicide Application | None | Ia SEED-0.5% SW* |
| None | — | — | 0 | 0 |
| IIa | .002 | PRE | 7 | 2 |
| | .004 | PRE | 7 | 3 |
| IIb | .25 | PRE | 5 | 2 |
| | .5 | PRE | 6 | 2 |
| EPTAM** | 6 | PPI | 10 | 7.5 |

*% SW = percent seed weight
**EPTAM = S-ethyl dipropylthiocarbamate

EXAMPLE 2

| | Wheat Injury Rating (After 7 Weeks) | | |
|---|---|---|---|
| | Conc. | | Antidote |
| Herbicide | in soil ppb | None | Ia SEED-0.5% SW |
| None | — | 0 | 0 |
| IIc | .25 | 0 | 0 |
| | .5 | 2 | 0 |
| | 1.0 | 4** | 0 |
| | 1.5 | 6** | 4* |
| | 2 | 6.5** | 4** |
| | 3 | 6.5** | 4.5** |

*partially headed out
**not headed out
(all other treatments headed out)

EXAMPLE 3

| | | Crop Injury Rating (After 5 Weeks) | | | | |
|---|---|---|---|---|---|---|
| | | | Antidotes | | | |
| Herbicide | | | Ia(2 kg/ha) | | Ic(0.5 kg/ha) | |
| PRE | kg/ha | None | ROW | PPI | ROW | PPI |
| Corn | | | | | | |
| None | — | 0 | 0 | 0 | 0 | 0 |
| IIa | 0.062 | 9.5 | 8.5 | 8.2 | 8.0 | 8.2 |
| IIb | 0.5 | 8.5 | 3.0 | 4.3 | 3.0 | 3.0 |
| Soybeans | | | | | | |
| None | | 0 | 0 | 0 | 0 | 0 |
| IIa | 0.062 | 9 | 9 | 9 | 9 | 9 |
| IIb | 0.5 | 9 | 9 | 9 | 9 | 9 |
| Rice | | | | | | |
| None | | 0 | 0 | 0 | 0 | 0 |
| IIa | 0.062 | 9.5 | 9.5 | 8.8 | 8.0 | 7.5 |
| IIb | 0.5 | 5 | 4.5 | 5 | 5.5 | 6.2 |

EXAMPLE 4

| | | Corn Injury Rating (After 4 Weeks) | | | | | | |
|---|---|---|---|---|---|---|---|---|
| | | Antidotes | | | | | | |
| | kg/ | | SEED (.5% SW) | | ROW (2 kg/ha) | | POST (2 kg/ha) | |
| Herb. | ha | None | Ia | IaK+ | Ia | IaK+ | Ia | IaK+ |
| PRE | | | | | | | | |
| None | — | 0 | 0 | 0 | 0 | 0 | 0 | 0 |
| IIa | 0.031 | 10 | 7 | 7 | 8 | 10 | 10 | 10 |
| | 0.125 | 10 | 7 | 7 | 9 | 10 | 10 | 10 |
| | 0.5 | 10 | 8 | 8 | 10 | 10 | 10 | 10 |
| IIb | 0.031 | 0 | 0 | 0 | 0 | 0 | 0 | 0 |
| | 0.125 | 5 | 2 | 0 | 3 | 0 | 4 | 4 |
| | 0.5 | 7 | 3 | 2 | 4 | 6 | 7 | 5 |
| POST | | | | | | | | |
| None | — | 0 | 0 | 0 | 0 | 0 | 0 | 0 |
| IIa | 0.031 | 10 | 5 | 5 | 10 | 10 | 8 | 4 |
| | 0.125 | 10 | 8 | 7 | 10 | 10 | 10 | 8 |
| | 0.5 | 10 | 9 | 8 | 10 | 10 | 10 | 10 |
| IIb | 0.031 | 0 | 0 | 0 | 0 | 0 | 0 | 0 |
| | 0.125 | 2 | 0 | 0 | 3 | 3 | 0 | 0 |
| | 0.5 | 5 | 2 | 2 | 4 | 4 | 2 | 0 |

IaK+ = potassium salt of Ia

EXAMPLE 5

| | | Corn Injury Rating (After 4 Weeks) | | | | | | |
|---|---|---|---|---|---|---|---|---|
| | | | Antidotes | | | | | |
| | | | Ia | | | Ib | | |
| Herb. | kg/ha | None | PPI 2 kg/ha | SEED 0.5% SW | PRE 2 kg/ha | PPI 0.5 kg/ha | SEED 0.25 SW | PRE 0.5 kg/ha |
| PPI | | | | | | | | |
| None | — | 0 | 0 | 0 | — | 0 | 2 | — |
| IIb | 0.125 | 3 | 2 | 2 | — | 3 | 4 | — |
| | 0.25 | 4 | 3 | 2 | — | 2.5 | 3 | — |
| | 0.5 | 4 | 4.5 | 3 | — | 3 | 3 | — |
| PRE | | | | | | | | |
| None | — | 0 | 0 | 0 | 0 | 0 | 0 | 0 |

-continued

| | | Corn Injury Rating (After 4 Weeks) | | | | | | |
|---|---|---|---|---|---|---|---|---|
| | | Antidotes | | | | | | |
| | | | Ia | | | Ib | | |
| Herb. | kg/ha | None | PPI 2 kg/ha | SEED 0.5% SW | PRE 2 kg/ha | PPI 0.5 kg/ha | SEED 0.25 SW | PRE 0.5 kg/ha |
| IIb | 0.125 | 2 | 0 | 0 | 2 | 0 | 3 | 2 |
| | 0.25 | 4 | 2.5 | 2.5 | 3 | 3 | 3 | 3 |
| | 0.5 | 3.5 | 3 | 2.5 | 5 | 3 | 3 | 3 |
| EARLY POST | | | | | | | | |
| None | — | 0 | 0 | 0 | — | 0 | 0 | — |
| IIb | 0.125 | 0 | 2 | 0 | — | 0 | 0 | — |
| | 0.25 | 2 | 3 | 2 | — | 2 | 2 | — |
| | 0.5 | 5 | 4 | 3 | — | 2 | 3 | — |
| LATE POST | | | | | | | | |
| None | — | 0 | — | 0 | — | — | 0 | — |
| IIb | 0.125 | 0 | — | 0 | — | — | 3 | — |
| | 0.25 | 5.5 | — | 0 | — | — | 0 | — |
| | 0.5 | 0 | — | 0 | — | — | 0 | — |

EXAMPLE 6

| | | Corn Injury Rating Antidote Ia (After 3 Weeks) | | | | | | |
|---|---|---|---|---|---|---|---|---|
| | | Corn | | | | Nutsedge | | |
| Herb. | kg/ha | None | SEED 0.5% SW | ROW 2 kg/ha | POST 2 kg/ha | None | ROW 2 kg/ha | POST 2 kg/ha |
| PRE | | | | | | | | |
| None | — | 0 | 0 | 0 | 0 | 0 | 0 | 0 |
| IIb | .062 | 3.5 | 2.5 | 2 | 3.5 | 10 | 10 | 10 |
| | .25 | 8 | 4 | 5.5 | 7.5 | 10 | 10 | 10 |
| | 1 | 8 | 5.5 | 6.5 | 8 | 10 | 10 | 10 |
| POST | | | | | | | | |
| None | — | 0 | — | 0 | 0 | 0 | 0 | 0 |
| IIb | .016 | 0 | — | 0 | 0 | 6.5 | 7.5 | 8.5 |
| | .062 | 1 | — | 0 | 0 | 9 | 9 | 8 |
| | .25 | 2.5 | — | 2 | 2 | 9.5 | 9 | 9 |
| | 1 | 7 | — | 5 | 5.5 | 10 | 10 | 10 |

EXAMPLE 7

| | | Corn Injury Rating Antidote Ic (After 3 Weeks) | | | | | | |
|---|---|---|---|---|---|---|---|---|
| | | Corn | | | | Nutsedge | | |
| Herb. | kg/ha | None | SEED 0.25% SW | ROW 0.5 kg/ha | POST 0.5 kg/ha | None | ROW 0.5 kg/ha | POST 0.5 kg/ha |
| PRE | | | | | | | | |
| None | — | 0 | 0 | 0 | 0 | 0 | 0 | 0 |
| IIb | .062 | 3.5 | 0 | 1 | 3.5 | 10 | 10 | 10 |
| | .25 | 8 | 2.5 | 3.5 | 7 | 10 | 10 | 10 |
| | 1 | 8 | 5 | 4 | 7.5 | 10 | 10 | 10 |
| POST | | | | | | | | |
| None | — | 0 | — | 0 | 0 | 0 | 0 | 0 |
| IIb | .016 | 0 | — | 0 | 0 | 6.5 | 6.5 | 7 |
| | .062 | 1 | — | 0 | 1 | 9 | 8 | 8.5 |
| | .25 | 2.5 | — | 2 | 2 | 9.5 | 8.5 | 10 |
| | 1 | 7 | — | 3.5 | 4.5 | 10 | 10 | 10 |

EXAMPLE 8

| | | Corn Injury Rating (After 3 Weeks) Antidote-Post at Spike Stage | | |
|---|---|---|---|---|
| Herbicide Post-Spike Stage | kg/ha | None | Ia 2 kg/ha | Ic 0.5 kg/ha |
| None | — | 0 | 0 | 0 |
| IIb | 0.25 | 6 | 4.2 | 3 |

-continued

| Herbicide Post-Spike Stage | kg/ha | Corn Injury Rating (After 3 Weeks) Antidote-Post at Spike Stage None | Ia 2 kg/ha | Ic 0.5 kg/ha |
|---|---|---|---|---|
| | 0.5 | 6.8 | 4.5 | 4.2 |
| | 1.0 | 7.8 | 6.2 | 5.5 |

EXAMPLE 9

| Herbicide | kg/ha | Crop Injury Rating (After 5 Weeks) Antidote Ib None | Seed 0.125% SW | Row 2 kg/ha | Post 0.5 kg/ha |
|---|---|---|---|---|---|
| PRE | | | (CORN) | | |
| None | — | 0 | 3 | 0 | — |
| IIa | 0.062 | 9 | 7.5 | 8 | — |
| IIb | 0.125 | 4 | 1 | 0 | — |
| | | | (SORGHUM) | | |
| None | — | 0 | 0 | 0 | — |
| IIa | 0.062 | 9.5 | 5.5 | 5.5 | — |
| IIb | 0.125 | 0 | 0 | 0 | — |
| | | | (SOYBEANS) | | |
| None | — | 0 | 0 | 0 | — |
| IIa | 0.062 | 9 | 9 | 9 | — |
| IIb | 0.125 | 9 | 9 | 9 | — |
| POST | | | (WHEAT) | | |
| None | — | 0 | 0 | 0 | 0 |
| IIb | 0.125 | 2.5 | 0 | 0 | 0 |
| | | | (CORN) | | |
| None | — | — | 0 | 0 | 0 |
| IIb | 0.125 | 2 | 0 | 0 | 2 |
| | | | (SORGHUM) | | |
| None | — | 0 | 0 | 0 | 0 |
| IIb | 0.125 | 2 | 0 | 1 | 2 |
| | | | (SOYBEANS) | | |
| None | — | 0 | 0 | 0 | 0 |
| IIb | 0.125 | 7 | 7 | 7 | 7 |

EXAMPLE 10

| Herbicide | kg/ha | Wheat Injury Rating (After 4 Weeks) Antidotes None | SEED .5% SW Ia | SEED .5% SW IaK+ | ROW 2 kg/ha Ia | ROW 2 kg/ha IaK+ | POST 2 kg/ha Ia | POST 2 kg/ha IaK+ |
|---|---|---|---|---|---|---|---|---|
| PRE | | | | | | | | |
| None | — | 0 | 0 | 0 | 0 | 0 | 0 | 0 |
| IIa | 0.031 | 0 | 0 | 0 | 0 | 0 | 0 | 0 |
| | 0.125 | 3 | 0 | 0 | 0 | 0 | 0 | 0 |
| | 0.5 | 7 | 4 | 4 | 5 | 5 | 6 | 7 |
| IIb | 0.031 | 0 | 0 | 0 | 0 | 0 | 0 | 0 |
| | 0.125 | 0 | 0 | 0 | 0 | 0 | 0 | 0 |
| | 0.5 | 0 | 0 | 0 | 0 | 0 | 0 | 0 |
| POST | | | | | | | | |
| None | — | 0 | 0 | 0 | 0 | 0 | 0 | 0 |
| IIa | 0.031 | 0 | 0 | 0 | 0 | 0 | 0 | 0 |
| | 0.125 | 5 | 0 | 0 | 4 | 5 | 2 | 0 |
| | 0.5 | 7 | 3 | 4 | 6 | 7 | 8 | 6 |
| IIb | 0.031 | 0 | 0 | 0 | 0 | 0 | 0 | 0 |
| | 0.125 | 0 | 0 | 0 | 0 | 0 | 0 | 0 |
| | 0.5 | 0 | 0 | 0 | 0 | 0 | 0 | 0 |

EXAMPLE 11

Corn, variety Pioneer L3369, was planted in the field on Matapeake silt loam soil in rows about 60 cm apart with 15 cm between plants in the row. Antidotes and herbicides were applied postemergence when the corn was in the three leaf growth stage. For spraying, the treatment components were dissolved in 5% acetone to which 0.2% Tween-20 had been added. The acetone-Tween-20 solvent was sprayed on similar plots for comparison.

The response of corn to the treatments was evaluated 5 weeks after spraying by height measurements and by visual observations as recorded in the following table:

| Herbicide Post | kg/ha | Injury Response (After 5 Weeks) Antidote - Post None | Ia 0.5 kg/ha | IaK+ 0.3 kg/ha | IaK+ 1 kg/ha |
|---|---|---|---|---|---|
| None | — | 0 | 0 | 0 | 0 |
| IIa | 0.011 | 6.5 | 6.5 | 5.5 | 2.5 |
| IIb | 0.2 | 5 | 3.5 | 3 | 2.5 |

*IaK+—potassium salt of Ia.

EXAMPLE 12

Postemergent Weed Control With Herbicide - Antidote Combinations

Corn and common weed seeds were planted together in 7" pots with Jiffy Mix (Jiffy Products of America, West Chicago, Ill.; a peat moss-vermiculite containing pot mix): gravel (sand blast #3) 50:50, in a growth room with 18 hour photo period, 75°-80° F. day and 70° F. night temperatures. The pots were watered with tap water for 1 to 2 weeks after planting and then with a modified Hoagland solution in the morning and water in the evening. Solutions of herbicide II*a* and antidote I*a* were prepared separately in AGWET-WGT (60:40)*. The postemergence herbicide treatment was made at two weeks after planting; the postemergent antidote treatment was made two days prior to the herbicide application.

| Plant | Rate of Herbicide IIa (POST) lbs/acre | Rate of Antidote Ia (POST) lbs/acre | Injury Rating (2 weeks) |
|---|---|---|---|
| Corn | 0 | 0 | 0 |
| Corn | 0.01 | 0 | 10 |
| Corn | 0.01 | 5 | 3 |
| Morningglory | 0.01 | 0 | 9 |
| Morningglory | 0.01 | 5 | 9 |
| Sickle Pod | 0.01 | 0 | 8 |
| Sickle Pod | 0.01 | 5 | 8 |
| Velvetleaf | 0.01 | 0 | 9 |
| Velvetleaf | 0.01 | 5 | 9 |
| Indigo | 0.01 | 0 | 9 |
| Indigo | 0.01 | 5 | 9 |
| Foxtail | 0.01 | 0 | 5 |
| Foxtail | 0.01 | 5 | 4 |

The herbicides and antidotes described herein can be formulated in a number of ways:

(a) the antidote can be formulated for application directly to the crop seed;

(b) the antidote and herbicide may be formulated separately and applied separately or applied simultaneously in an appropriate weight ratio as a tank mix; or (c) the antidote and herbicide may be formulated together in the proper weight ratio.

Procedures useful for formulating the herbicides and antidotes described herein are described in U.S. Pat. Nos. 4,127,405, 4,169,719, 3,564,768, 3,749,566, 4,070,389, 4,021,224, 4,124,376, 4,137,070 and 4,115,099, the disclosures of which are hereby incorporated by reference. The following examples are illustrative of the various formulation techniques which can be used.

EXAMPLE 13

Oil Suspension 1,8-naphthalic anhydride—25%
polyoxyethylene sorbitol hexaoleate—5%
highly aliphatic hydrocarbon oil—70%

The ingredients are ground together in a sand mill until the solid particles have been reduced to under about 5 microns. The resulting suspension may be applied directly, but preferably after being extended with oils or emulsified in water.

EXAMPLE 14

High Strength Concentrate 1,8-naphthalic anhydride—98.5%
silica aerogel—0.5%
synthetic amorphous fine silica—1.0%

The ingredients are blended and ground in a hammer mill to produce a high strength concentrate, essentially all passing a U.S. Ser. No. 50 sieve (0.3 mm openings). This material may then be formulated in a variety of ways.

EXAMPLE 15

Emulsifiable Concentrate

N,N-diallyl-2,2-dichloroacetamide—30%
blend of oil soluble sulfonates and polyoxyethylene ethers—4%
xylene—66%

The ingredients are combined and stirred with gentle warming to speed solution. A fine screen filter is included in the packaging operation to insure the absence of any extraneous undissolved material in the product.

EXAMPLE 16

Wettable Powder 1,8-naphthalic anhydride—40%
dioctyl sodium sulfosuccinate—1.5%
sodium ligninsulfonate—3%
low viscosity methyl cellulose—1.5%
attapulgite—54%

The ingredients are thoroughly blended, passed through an air mill to produce an average particle size under 15 microns, reblended, and sifted through a U.S. Ser. No. 50 sieve (0.3 mm opening) before packaging.

EXAMPLE 17

Wettable Powder (a) 2,5-dichloro-N-[(4,6-dimethoxypyrimidin-2-yl)-aminocarbonyl]benzenesulfonamide—3%
(b) 1,8-naphthalic anhydride—50%
dioctyl sodium sufosuccinate—1.5%
sodium ligninsulfonate—3%
low viscosity methyl cellulose—1.5%
attapulgite—41%

The ingredients are thoroughly blended, passed through an air mill to produce an average particle size under 15 microns, reblended, and sifted through a U.S. Ser. No. 50 sieve (0.3 mm opening) before packaging.

EXAMPLE 18

Wettable Powder (a) 2-chloro-N-[(4-methoxy-6-methyl-1,3,5-triazin-2-yl)aminocarbonyl]benzenesulfonamide—2%
(b) 1,8-naphthalic anhydride—40%
sodium alkylnaphthalenesulfonate—2%
low viscosity methyl cellulose—2%
diatomaceous earth—54%

The ingredients are blended, coarsely hammer milled and then air milled to produce particles essentially all below 10 microns in diameter. The product is reblended before packaging.

EXAMPLE 19

Wettable Powder 2-chloro-N-[(4-methoxy-6-methyl-1,3,5-triazin-2-yl)-aminocarbonyl]benzenesulfonamide—80%
sodium alkylnaphthalenesulfonate—2%
sodium ligninsulfonate—2%
synthetic amorphous silica—3%
kaolinite—13%

The ingredients are blended and coarsely ground in a hammer mill to produce particles essentially all below 100 microns in size. The composition is then reblended, sifted through a U.S. Ser. No. 50 sieve (0.3 mm opening) and packaged.

EXAMPLE 20

Solution

N,N-diallyl-2,2-dichloroacetamide—20%
octylphenoxypolyethoxyethanol—5%
high boiling petroleum distillate—75%

The ingredients are combined and stirred to produce a solution which can be applied directly or after dilution with additional water.

EXAMPLE 21

Wettable Powder 2,5-dichloro-N-[(4,6-dimethoxypyrimidin-2-yl)-aminocarbonyl]benzenesulfonamide—50%
sodium alkylnaphthalenesulfonate—2%
low viscosity methyl cellulose—2%
diatomaceous earth—46%

The ingredients are blended, coarsely hammer milled and then air milled to produce particles essentially all below 10 microns in diameter. The product is reblended before packaging.

EXAMPLE 22

Wettable Powder of Example 16—40 parts
Wettable Powder of Example 19—1 part

A tank mix is made by adding these formulations in the proportions given to a stirred mixing tank containing enough water to give a convenient concentration for field application. The mixture can be sprayed using conventional spraying techniques.

EXAMPLE 23

Concentrate of Example 15—50 parts
Wettable Powder of Example 21—1 part

A tank mix is made by adding these formulations in the proportions given to a stirred mixing tank containing sufficient water to give a convenient tank concentration for the use intended. The mixture can be sprayed using conventional spraying techniques.

EXAMPLE 24

Slurry Seed Coat

α-(cyanomethoxyimino)benzacetonitrile—25%
calcium ligninsulfonate—4%
trimethyl nonyl polyethylene glycol ether—4%
Rhodamine B—1%
permanent red 2 B, calcium salt, extended on Blanc Fixe—1%
diatomaceous earth—65%

The liquid surfactant and active ingredient are sprayed on the diatomaceous earth, the other ingredients are then added and thoroughly mixed together in an efficient blender. The mixture is then coarsely hammer milled and passed through a fluid mill to produce particles of active ingredient that are less than 10 microns in diameter. The product is reblended before packaging. (Product is used by making about a 30–40% slurry in water and applying the slurry to seed in a commercial seed treater.)

EXAMPLE 25

Dust Seed Coat 1,8-naphthalic anhydride—75%
permanent red 2 B, calcium salt, extended on Blanc Fixe—5%
diatomaceous earth—20%

The ingredients are blended, coarsely hammer milled and passed through a fluid mill to produce particles of active ingredient that are all below 10 microns in diameter. The product is reblended before packaging. (Product is used by dusting on seed at rates of 1–800 gms/100 kg.)

What is claimed is:

1. An herbicidal composition comprising an herbicidally effective amount of an herbicidal compound selected from 2-chloro-N-[(4-methoxy-6-methyl-1,3,5-triazin-2-yl)aminocarbonyl]benzenesulfonamide and 2,5-dichloro-N-[(4,6-dimethoxypyrimidin-2-yl)aminocarbonyl]benzenesulfonamide and a non-phytotoxic antidotally effective amount of an antidotal compound selected from 1,8-naphthalic anhydride, α-(cyanomethoxyimino)benzacetonitrile, and N,N-diallyl-2,2-dichloroacetamide.

2. A composition of claim 1 where the antidotal compound is 1,8-naphthalic anhydride.

3. A composition of claim 1 where the antidotal compound is α-(cyanomethoxyimino)benzacetonitrile.

4. A composition of claim 1 where the antidotal compound is N,N-diallyl-2,2-dichloroacetamide.

5. A composition of claim 1 where the ratio of herbicidal compound to antidotal compound is in the range of 1:200 to 10,000:1.

6. A method of controlling weeds and protecting cereal crop plants comprising applying to the locus thereof an herbicidally effective amount of a composition of claim 1.

7. A method of protecting cereal crop plants from injury due to an herbicidal compound selected from 2-chloro-N-[(4-methoxy-6-methyl-1,3,5-triazin-2-yl)aminocarbonyl]benzenesulfonamide and 2,5-dichloro-N-[(4,6-dimethoxypyrimidin-2-yl)aminocarbonyl]benzenesulfonamide comprising combining application of an herbicidally effective amount of said herbicidal compound to the locus of said crop plants with application of a non-phytotoxic antidotally effective amount of an antidotal compound selected from 1,8-naphthalic anhydride, α-(cyanomethoxyimino)benzacetonitrile, and N,N-diallyl-2,2-dichloroacetamide to the crop seed, to the crop plant or to the locus of the crop plant.

8. A method according to claim 7 wherein said antidotal compound is applied to the soil in which crop seeds are to be planted.

9. A method according to claim 7 wherein said antidotal compound is applied to the soil in which crop seeds have been planted prior to emergence of the crop plants.

10. A method according to claim 7 wherein said antidotal compound is applied to the surface of the crop plants and to the soil surrounding said crop plants.

11. A method according to claim 7 wherein crop seeds are coated with said antidotal compound prior to planting.

12. A method according to claim 7 wherein said antidotal compound is applied to exposed crop seeds in furrow prior to completion of planting.

13. A method according to claim 7 wherein said antidotal compound is 1,8-naphthalic anhydride.

14. A method according to claim 7 wherein said antidotal compound is α-(cyanomethoxyimino)benzacetonitrile.

15. A method according to claim 7 wherein said antidotal compound is N,N-diallyl-2,2-dichloroacetamide.

* * * * *